United States Patent
Seo et al.

(10) Patent No.: US 11,512,318 B2
(45) Date of Patent: Nov. 29, 2022

(54) **METHOD FOR PRODUCING 3-FUCOSYLLACTOSE USING *CORYNEBACTERIUM GLUTAMICUM***

(71) Applicants: SEOUL NATIONAL UNIVERSITY R&DB FOUNDATION, Seoul (KR); ADVANCED PROTEIN TECHNOLOGIES CORP., Suwon-si (KR)

(72) Inventors: Jin-Ho Seo, Seoul (KR); Sang-Min Jung, Suwon-si (KR); Do-Haeng Lee, Incheon (KR); Hyeong-Do Jeon, Incheon (KR)

(73) Assignees: SEOUL NATIONAL UNIVERSITY R&DB FOUNDATION, Seoul (KR); ADVANCED PROTEIN TECHNOLOGIES CORP., Suwon-si (KR)

( * ) Notice: Subject to any disclaimer, the term of this patent is extended or adjusted under 35 U.S.C. 154(b) by 0 days.

(21) Appl. No.: 16/606,921

(22) PCT Filed: Apr. 20, 2018

(86) PCT No.: PCT/KR2018/004597
§ 371 (c)(1),
(2) Date: Nov. 26, 2019

(87) PCT Pub. No.: WO2018/194411
PCT Pub. Date: Oct. 25, 2018

(65) Prior Publication Data
US 2020/0080095 A1  Mar. 12, 2020

(30) Foreign Application Priority Data

Apr. 21, 2017 (KR) .................. 10-2017-0051871
Apr. 20, 2018 (KR) .................. 10-2018-0045845

(51) Int. Cl.
*C12P 19/04* (2006.01)
*C12N 9/12* (2006.01)
*C12N 9/90* (2006.01)
*C12N 15/77* (2006.01)

(52) U.S. Cl.
CPC .............. *C12N 15/77* (2013.01); *C12N 9/12* (2013.01); *C12N 9/90* (2013.01); *C12P 19/04* (2013.01); *C12Y 101/01132* (2013.01)

(58) Field of Classification Search
CPC ...... C12N 15/77; C12N 9/1051; C12N 15/70; C12N 9/10; C12Y 101/01271; C12Y 402/01047; C12Y 101/01132; C12Y 204/01; C12P 19/04; C12P 19/00; C12P 19/02
USPC ........................................................... 435/74
See application file for complete search history.

(56) References Cited

U.S. PATENT DOCUMENTS 6,875,591 B1 * 4/2005 Koizumi et al. ........ C12P 19/30
435/89

FOREIGN PATENT DOCUMENTS

| EP | 3315610 A1 * | 5/2018 | .............. C12P 19/18 |
|---|---|---|---|
| JP | 2014-506474 A | 3/2014 | |
| KR | 10-2012-0122098 A | 11/2012 | |
| KR | 10-1544184 B1 | 8/2015 | |
| KR | 10-1648352 B1 | 8/2016 | |
| KR | 1020160012803 A | 8/2017 | |
| WO | WO2015150328 * | 8/2015 | |
| WO | 2016/040531 A1 | 3/2016 | |
| WO | 2017/188684 A1 | 11/2017 | |

OTHER PUBLICATIONS

Chin et al. Bioprocess Biosyst Eng. Jun. 2013;36(6):pp. 749-756.*
EP3315610 PDF 2016 pp. 1-41.*
NCBI Genbank Accession No. CP007794.1, Jul. 26, 2016.
Chin et al., "Metabolic engineering of Corynebacterium glutamicum to produce GDP-1-fucose from glucose and mannose", Bioprocess Biosyst Eng, 2013, vol. 36, pp. 749-756.
GenBank Accession No. CR626927; Bacteroides fragilis NCTC P343, complete genome, Cerdeno-Tarraga, A.M.,et al. "Extensive DNA inversions B. fragilis genome control variable gene expression"; Science 307 (5714), ( 2 pages total) 2005, pp. 1463-1465, 343, complete genome; Genbank Accession No. CR626927.1; (2 pages total).

* cited by examiner

*Primary Examiner* — Tekchand Saidha
*Assistant Examiner* — Mohammad Y Meah
(74) *Attorney, Agent, or Firm* — Sughrue Mion, PLLC

(57) ABSTRACT

Disclosed is a method for producing 3-fucosyllactose using a wild *Corynebacterium glutamicum* strain. In addition, using the *Corynebacterium glutamicum* strain, which is a GRAS strain, 3-fucosyllactose can be produced at a high concentration, high yield and high productivity.

4 Claims, 4 Drawing Sheets
Specification includes a Sequence Listing.

METHOD FOR PRODUCING 3-FUCOSYLLACTOSE USING *CORYNEBACTERIUM GLUTAMICUM*

SEQUENCE LISTING

The Sequence Listing submitted in text format (.txt) filed on Nov. 26, 2019, named "SequenceListinq.txt", created on Nov. 11, 2019 (12.2 KB), is incorporated herein by reference.

TECHNICAL FIELD

The present invention relates to a method for producing fucosyllactose from a variant microorganism for producing 3-fucosyllactose using a wild *Corynebacterium glutamicum* strain, glucose and lactose, and more particularly to a method for producing 3-fucosyllactose using a recombinant *Corynebacterium glutamicum* (*C. glutamicum*) obtained by introducing, into *Corynebacterium glutamicum*, phosphomannomutase (ManB), mannose-1-phosphate guanylyltransferase (ManC), GDP-D-mannose-4,6-dehydratase (Gmd), GDP-L-fucose synthase (WcaG), α-1,3-fucose transferase and a variant lac operon, from which lacZ is removed.

BACKGROUND ART

Human breast milk contains 200 or more kinds of human milk oligosaccharides (HMOs) having different structures which are present at a considerably higher concentration (5 to 15 g/L) than other mammals. Such HMO has functions essential for infants such as a prebiotic effect, the effect of inhibiting adhesion of pathogens on the intestines and the effect of modulating the immune regulation system.

Meanwhile, among HMOs, 3-fucosyllactose is reported to be a core HMO involved in a variety of biological activities. Methods of producing 3-fucosyllactose include direct extraction from breast milk and chemical or enzymatic synthesis. However, direct extraction has drawbacks of limited breast milk supply and low productivity and chemical synthesis has drawbacks of expensive substrates, low stereo-selectivity and production yield, the use of toxic organic solvents and the like. In addition, enzymatic synthesis has drawbacks in that GDP-L-fucose used as a fucose donor is very expensive and purification of fucosyltransferase is expensive.

As such, it is difficult to apply direct extraction and chemical or enzymatic production to the mass-production of fucosyllactose. However, biotechnological production using microorganisms is in the spotlight as a method for producing 3-fucosyllactose having the potential to be developed into a functional food and pharmaceutical material since it is capable of producing a large amount of fucosyllactose from a cheap substrate through a simple process.

Meanwhile, conventional methods for producing 3-fucosyllactose using microorganisms are mostly production techniques using recombinant *E. coli*. *E. coli*, which is used for experiments, is strongly considered to be a harmful bacterium by consumers although it is not actually a pathogen and incurs high costs of separation and purification because the cell membrane component can act as an endotoxin. For this reason, it is difficult to use *E. coli* as a host cell to produce 3-fucosyllactose.

Korean Patent No. 10-1544184 (Registration Date: Aug. 21, 2015) relates to a mutant microorganism for producing 2'-fucosyllactose and a method for producing 2'-fucosyllactose using the same, and discloses a variant microorganism obtained by introducing or amplifying one or more genes selected from the group consisting of a gene introduced with an operon, in which lacZ is modified or removed, and a gene encoding G6PDH (glucose-6-phosphate dehydrogenase) and GSK (guanosine-inosine kinase), and a method for producing 2'-fucosyllactose using the same.

Korean Patent No. 10-1648352 (Registration Date: Aug. 9, 2016) discloses a recombinant *E. coli* producing fucosyllactose in which at least one of genes encoding fucose isomerase (FucI), fuculose kinase (fucK) and fuculose 1-phosphate aldolase (FucA), which are fucose metabolic enzymes, is disrupted, and including, instead of a wild-type lac operon, a lac operon that includes a lacZ gene, a wild-type lacY gene and a wild-type lacA gene, encoding beta galactosidase having activity lower than wild beta galactosidase, or a lac operon that is completely free of a wild-type lacZ gene and includes only a wild-type lacY gene and a wild-type lacA gene, and a method for producing fucosyllactose using the same, which can produce 2- or 3-fucosyllactose with high productivity.

DISCLOSURE

Technical Problem

Therefore, the present invention has been made in view of the above problems, and it is one object of the present invention to develop and provide a method for producing 3-fucosyllactose at a high concentration, high yield and high productivity while using, as a host cell that produces fucosyllactose, which is a food and/or medicinal material, *Corynebacterium glutamicum*, which is safer than *Escherichia coli*.

Technical Solution

In accordance with the present invention, the above and other objects can be accomplished by the provision of recombinant *Corynebacterium glutamicum* which is transformed to express α-1,3-fucosyltransferase, is transformed to express GDP-D-mannose-4,6-dehydratase, is transformed to express GDP-L-fucose synthase, and is transformed to express lactose permease, wherein the recombinant *Corynebacterium glutamicum* has phosphomannomutase and GTP-mannose-1-phosphate guanylyltransferase.

In the recombinant *Corynebacterium glutamicum* of the present invention, the α-1,3-fucosyltransferase is preferably encoded by an azoT gene. In this case, the azoT gene preferably has a nucleic acid sequence set forth in SEQ ID NO: 5.

In the recombinant *Corynebacterium glutamicum* of the present invention, the recombinant *Corynebacterium glutamicum* is preferably transformed to overexpress phosphomannomutase and is transformed to overexpress GTP-mannose-1-phosphate guanylyltransferase.

In accordance with another aspect, provided is a method of producing 3-fucosyllactose including culturing, in a medium supplemented with lactose, recombinant *Corynebacterium glutamicum*, which is transformed to express α-1,3-fucosyltransferase, is transformed to express GDP-D-mannose-4,6-dehydratase, is transformed to express GDP-L-fucose synthase, and is transformed to express lactose permease, wherein the recombinant *Corynebacterium glutamicum* has phosphomannomutase and GTP-mannose-1-phosphate guanylyltransferase.

In the method of producing 3-fucosyllactose, the medium may further include glucose. In this case, the production of the 3-fucosyllactose may be carried out by batch culture or fed-batch culture including the further supply of glucose or lactose.

Advantageous Effects

According to the present invention, it is possible to produce 3-fucosyllactose using a *Corynebacterium glutamicum* strain, which is a GRAS strain. 3-fucosyllactose can be produced more safely than conventional *Escherichia coli*. In addition, using the *Corynebacterium glutamicum* strain according to the present invention, 3-fucosyllactose can be produced at a high concentration, high yield and high productivity.

DESCRIPTION OF DRAWINGS

The above and other objects, features and other advantages of the present invention will be more clearly understood from the following detailed description taken in conjunction with the accompanying drawings, in which.

BEST MODE

Figure 1:
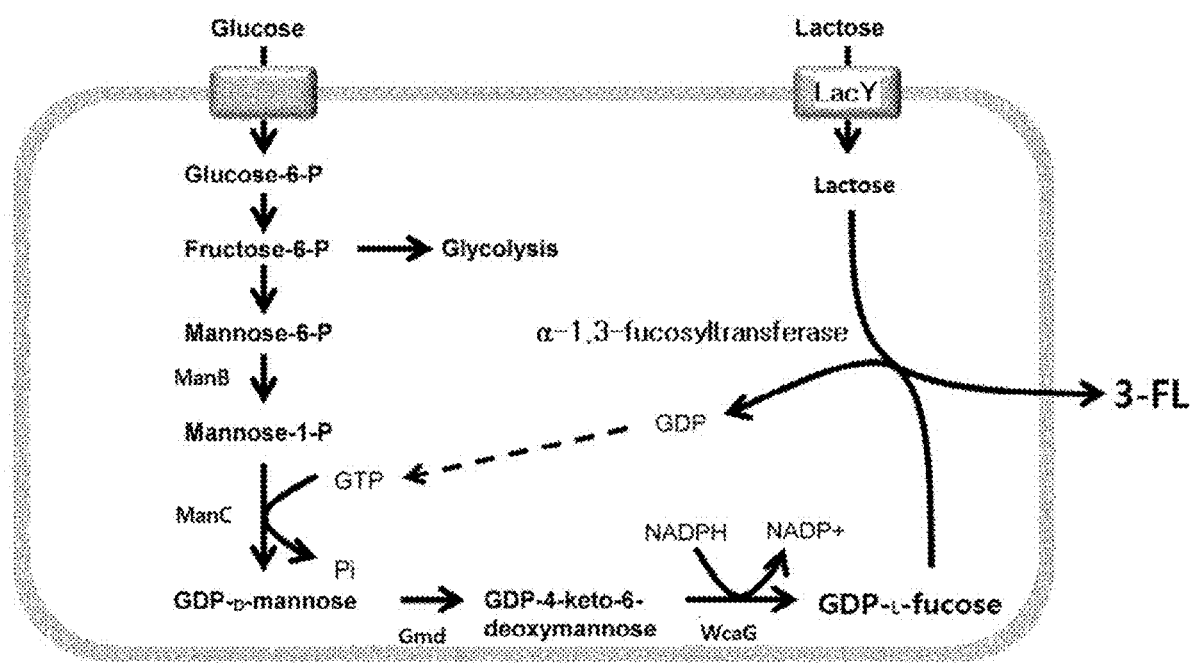
FIG. 1 is a schematic diagram showing a metabolic pathway introduced to bio-synthesize GDP-L-fucose and 3-fucosyllactose in a *Corynebacterium glutamicum* (*C. glutamicum*) strain.

In one aspect, the present invention is directed to recombinant *Corynebacterium glutamicum* which is transformed to express α-1,3-fucosyltransferase, is transformed to express GDP-D-mannose-4,6-dehydratase, is transformed to express GDP-L-fucose synthase, and is transformed to express lactose permease, wherein the recombinant *Corynebacterium glutamicum* has phosphomannomutase and GTP-mannose-1-phosphate guanylyltransferase.

The prevent inventors filed a patent application entitled "Method for producing 3-fucosyllactose using *Escherichia coli*" as Korean Patent Application No. 10-2016-0012803 (Feb. 2, 2016). However, it has been frequently indicated that producing 3-fucosyllactose for functional food additive applications using *Escherichia coli* may cause problems due to various safety associated with *Escherichia coli*. Accordingly, in accordance with the present invention, there is an attempt to produce 3-fucosyllactose using an alternative strain free of food safety problems.

The present invention adopts *Corynebacterium glutamicum* as a host cell producing 3-fucosyllactose. Unlike conventionally used *Escherichia coli*, this strain is considered to be a GRAS (generally recognized as safe) strain which does not produce endotoxins and is widely used for industrially producing amino acids and nucleic acids as food additives. Accordingly, *Corynebacterium glutamicum* is considered to be a stain suitable for the production of food and medicinal materials while advantageously eliminating customer fears about safety.

However, since *Escherichia coli* and *Corynebacterium glutamicum* have inherently different genetic properties, strategies different from those for *Escherichia coli* should be applied to *Corynebacterium glutamicum*. *Escherichia coli* and *Corynebacterium glutamicum* are the same in that external α-1,3-fucosyltransferase should be basically incorporated in order to produce 3-fucosyllactose. However, *Corynebacterium glutamicum* further requires the incorporation of GDP-D-mannose-4,6-dehydratase (Gmd), GDP-L-fucose synthase (this enzyme is called "GDP-4-keto-6-deoxy-D-mannose-3,5-epimerase-4-reductase" and is also simply referred to as "WcaG", and a gene encoding this enzyme is particularly referred to as "WcaG"), and lactose permease (Lacy). That is, *Escherichia coli* has genes encoding GDP-D-mannose-4,6-dehydratase (Gmd), GDP-L-fucose synthase (WcaG) and lactose permease (Lacy), but the *Corynebacterium glutamicum* strain has no genes encoding these enzymes, so it is necessary to incorporate such genes from an external source and express the same.

In this case, the gene encoding α-1,3-fucosyltransferase is preferably azoT derived from *Azospirillum brasilens*. In addition, genes encoding GDP-D-mannose-4,6-dehydratase (Gmd), GDP-L-fucose synthase (WcaG) and lactose permease (LacY) are preferably derived from *Escherichia coli*.

Meanwhile, the recombinant *Corynebacterium glutamicum* of the present invention is preferably transformed to overexpress phosphomannomutase, and is transformed to overexpress GTP-mannose-1-phosphate guanylyltransferase. *Corynebacterium glutamicum* possesses genes encoding phosphomannomutase (ManB) and GTP-mannose-1-phosphate guanylyltransferase (ManC), and can thus express the same. Therefore, there may be no need to incorporate genes encoding the enzymes, but the enzymes should be overexpressed for mass-production. For this reason, the present invention requires transformation of *Corynebacterium glutamicum* in order to overexpress the two enzymes.

Meanwhile, the actions of the enzymes can be understood from FIG. 1, and a detailed explanation thereof is thus omitted. It should be noted that lactose permease (LacY) is an enzyme involved in transporting lactose present outside the strain to the inside thereof. In the following example of the present invention, lacYA gene obtained by removing lacZ from a Lac operon of *Escherichia coli* is incorporated for experimentation. However, since incorporating a Lac operon in the present invention aims at introducing lactose, there is no need to incorporate lacA genes and it is sufficient simply for lacY genes to be incorporated.

Meanwhile, the term "expression" as used herein means incorporation and expression of external genes into strains in order to intentionally express enzymes that cannot be inherently expressed by the *Corynebacterium glutamicum* strain according to the present invention, and the term "overexpression" as used herein means overexpression that is induced by artificially increasing the amount of expressed enzyme in order to increase expression for mass-production, although the *Corynebacterium glutamicum* strain according to the present invention has genes encoding the corresponding enzyme and therefore can self-express the same.

Meanwhile, the present inventors can mass-produce 3-fucosyllactose, which is a breast milk oligosaccharide, in *Corynebacterium glutamicum* (*C. glutamicum*) through the transformation strategy described above.

Meanwhile, according to the present invention, genes encoding α-1,3-fucosyltransferase are, for example, encoded by azoT genes, wherein the azoT genes have the nucleic acid sequence set forth in SEQ ID NO: 5. In order to produce α-1,3-fucosyllactose, α-1,3-fucosyltransferase, which performs the production reaction of α-1,3-fucosyl-lactose using GDP-L-fucose and lactose as substrates is required (see FIG. 1). This enzyme is present in a variety of microorganisms, and in the present invention, azoT derived from *Azospirillum brasilense* is used. When α-1,3-fucosyltransferase having other origin was used, the production amount of 3-fucosyllactose was insignificant, but when the azoT gene was used, the yield of 3-fucosyllactose was significantly high.

Meanwhile, in another aspect, the present invention is directed to a method for producing 3-fucosyllactose including culturing the recombinant *Corynebacterium glutamicum* of the present invention in a medium supplemented with lactose. When the recombinant *Corynebacterium glutamicum* strain according to the present invention is used, 3-fucosyllactose can be produced at a high concentration, high yield and high productivity.

Meanwhile, regarding the method for producing 3-fucosyllactose according to the present invention, the medium preferably further includes glucose. By adding glucose to the medium, the growth of a strain can be facilitated, and 3-fucosyllactose can thus be produced at higher productivity.

Meanwhile, the method for producing 3-fucosyllactose according to the present invention is preferably carried out through batch culture or fed-batch culture that involves further supplying lactose. The detailed technologies associated with batch culture and fed-batch culture are well-known in the art and are not described herein.

Meanwhile, lactose permease was introduced into the strain *Corynebacterium glutamicum* of the present invention in order to incorporate lactose, which is the substrate for 3'-FL production, into strain cells. That is, in order to produce 3'-FL using *Corynebacterium glutamicum*, the strain of the present invention should be transformed with lactose permease capable of introducing lactose into strain cells. Accordingly, the strain of the present invention is transformed with this enzyme.

In this regard, the activity of lactose permease is usually inhibited by so-called "glucose repression" in the presence of glucose. As a result, the influx of lactose in the presence of glucose does not occur and thus 3-FL is not produced.

However, in the *Corynebacterium glutamicum* used in the present invention as a host strain for the production of 3'-FL, glucose repression does not occur and 3'-FL production is possible based on the inflow of lactose, even in the presence of glucose. As a result, the productivity of 3'-FL can be maximized.

Meanwhile, it can be identified from the following experiment of the present invention that the method for producing 3'-FL using the *Corynebacterium glutamicum* according to the present invention is based on a production pattern of non-growth-associated product formation.

The non-growth-associated product formation, in which the production of metabolites is independent of the growth of the host strain, does not further require the growth of the host strain for the production of metabolites, thus having an advantage of mass-producing large quantities of metabolites within a short time by culturing a large amount of host strain and incorporating a substrate therein. In addition, the non-growth-associated product formation has an advantage of maximizing productivity because the host strain used in the culture can be used repeatedly. Therefore, the method for producing 3'-FL established using *Corynebacterium glutamicum* according to the present invention is a method capable of maximizing the production of 3'-FL.

MODE FOR INVENTION

Hereinafter, the present invention will be described in more detail with reference to the following examples, but the scope of the present invention is not limited to the examples, and includes variations and technical concepts equivalent thereto.

Example 1: Production of Recombinant Strains and Plasmids

*Escherichia coli* TOP10 was used for cloning to produce plasmids and *Corynebacterium glutamicum* (*C. glutamicum*) ATCC 13032 is used to produce 3-fucosyllactose (3'-FL). Plasmids for expressing PVBCL expressing manB, manC and lacYA gene clusters developed in previous studies were used. In addition, a vector was constructed to express α-1,3-fucosyltransferase (azoT) in the plasmids for expressing pEGW expressing Gmd and WcaG genes. At this time, the origin of α-1,3-fucosetransferase (azoT) is *Azospirillum brasilense* ATCC 29145, and α-1,3-fucosetransferase (azoT) was inserted into the pEGW vector using a restriction enzyme of Sac1.

Meanwhile, gene sequences of ManB, ManC, Gmd, WcaG, lacYA and α-1,3-fucosetransferase (azoT), strains, plasmids and oligonucleotides used above are shown in Tables 1 to 3 below.

TABLE 1

| Gene name | SEQ. ID. NO |
| --- | --- |
| ManB | SEQ. ID. NO: 1 |
| ManC | SEQ. ID. NO: 2 |
| Gmd-WcaG | SEQ. ID. NO: 3 |
| lacYA | SEQ. ID. NO: 4 |
| azoT | SEQ. ID. NO: 5 |

TABLE 2

| | Related properties |
| --- | --- |
| Strains | |
| *E. coli* TOP10 | F−, mcrAΔ(mrr-hsdRMS-mcrBC) φ80lacZΔM15 ΔlacX74 recA1 araD139Δ(ara-leu)7697 galU galKrpsL(Str$^R$)endA1 nupG |
| *C. glutamicum* | Wild-type strain, ATCC 13032 |
| Plasmids | |
| pEKEx2 | Km$^R$; *C. glutamicum*/*E. coli* shuttle vector for regulated gene expression (P$_{tac}$, lacIq, pBL1, oriVC .g., oriVE.c.) |
| pVWEx2 | Tc$^R$; *C. glutamicum*/*E. coli* shuttle vector for regulated gene expression (P$_{tac}$, lacIq, pHM1519, oriVC .g., oriVE.c.) |
| pEGW | pEKEx2 + Gmd-WcaG |
| pVBCL | pVWEx2 + ManB + ManC + lacYA |
| pEGWA | pEGW + azoT |

TABLE 3

| Primer name | Sequence (5'→3') | SEQ. ID. NO: |
|---|---|---|
| F_inf_sac1_azoT | GCTTTCGGGGGTAAGAGC TCAAGGAGATATACAATG CTCGATCAGCGGACAAGC | SEQ. ID. NO: 6 |
| R_inf_sac1_azoT | CGGCCAGTGAATTCGAGC TCTTACAGCCGGCTCTCG ATCC | SEQ. ID. NO: 7 |

Example 2: Production of 3-Fucosyllactose Using Recombinant *Corynebacterium glutamicum*

(1) Culture Conditions and Methods

Seed culture was carried out using a test tube containing 5 mL of BHI (brain heart infusion) medium supplemented with appropriate antibiotics (kanamycin 25 μg/mL and tetracycline 5 μg/mL) at a temperature of 30° C. and a constant stirring rate of 250 rpm for 12 hours.

Batch culture was carried out at 30° C. in a 250 mL flask containing 100 mL (($NH_4)_2SO_4$ 20 g/L, urea 5 g/L, $KH_2PO_4$ 1 g/L, $K_2HPO_4$ 1 g/L, $MgSO_4$ 0.25 g/L, MOPS 42 g/L, $CaCl_2$) 10 mg/L, Biotin 0.2 mg/L, Protocatechuic acid 30 mg/L, $FeSO_4 7H_2O$ 10 mg/L, $MnSO_4 H_2O$ 10 mg/L, $ZnSO_4 7H_2O$ 1 mg/L, $CuSO_4$ 0.2 mg/L, $NiCl_2 6H_2O$ 0.02 mg/L, pH 7.0). The stirring rate was maintained at 250 rpm during culture. In case of batch culture, IPTG (isopropyl-ß-D-thiogalactopyranoside) and lactose were added such that final concentrations were adjusted to 1.0 mM and 10 g/L, respectively, when the optical density ($OD_{600}$) reached 0.8.

The fed-batch culture for high-concentration cell culture was carried out in a 2.5 L bioreactor (Kobiotech, Incheon, Korea) containing 1.0 L of a minimum medium supplemented with 40 g/L of glucose and appropriate antibiotics (25 μg/mL of kanamycin and 5 μg/mL of tetracycline).

After the glucose added at an initial stage was completely consumed, a feeding solution including 800 g/L of glucose was supplied at a rate of 5.7 g/L/h by a continuous feeding method. At the same time, IPTG and lactose were added such that final concentrations were adjusted to 1.0 mM and 10 g/L, respectively, in order to induce expression of tac-promotor-mediated genes and thereby produce 3-fucosyllactose.

When pH of the medium was lower than a set point during fermentation, 28% $NH_4OH$ was automatically supplied, and when the pH was higher than the set point, 2N HCl was added, so that the pH could be maintained within a predetermined range from 6.98 to 7.02. The pH of the medium was measured in real time using a pH electrode (Mettler Toledo, USA). The stirring rate and aeration rate were maintained at 1,000 rpm and 2 vvm to prevent lack of oxygen.

(2) Determination of Concentrations of Cells and Metabolites

The dried cell weight was determined by multiplying the optical density (OD) by a pre-measured transmutation constant of 0.3. The optical density (OD) was adjusted to the range of 0.1 to 0.5 by diluting a sample to an appropriate level, and the absorbance at 600 nm was measured using a spectrophotometer (Ultrospec 2000, Amersham Pharmacia Biotech, USA).

The concentrations of 3-fucosyllactose, lactose, lactate, glucose and acetic acid were measured using a high-performance liquid chromatography (HPLC) device (Agilent 1100LC, USA) equipped with a carbohydrate analysis column (Rezex ROA-organic acid, Phenomenex, USA) and a refractive index (RI) detector. 20 μl of the culture medium, diluted 10×, was analyzed using a column pre-heated to 60° C. 5 mM of a $H_2SO_4$ solution was used as a mobile phase at a flow rate of 0.6 mL/min.

(3) Production of 3'-Fucosyllactose Through Batch Culture

Recombinant *Corynebacterium glutamicum* introduced with a lac operon (lacYA) free of ManB, ManC, Gmd, WcaG, azoT and lacZ was batch-cultured in each flask in order to investigate 3-fucosyllactose productivity and fermentation characteristics. IPTG and lactose were added such that final concentrations were adjusted to 1.0 mM and 10 g/L, respectively, when optical density ($OD_{600}$) reached 0.8.

Figure 2:
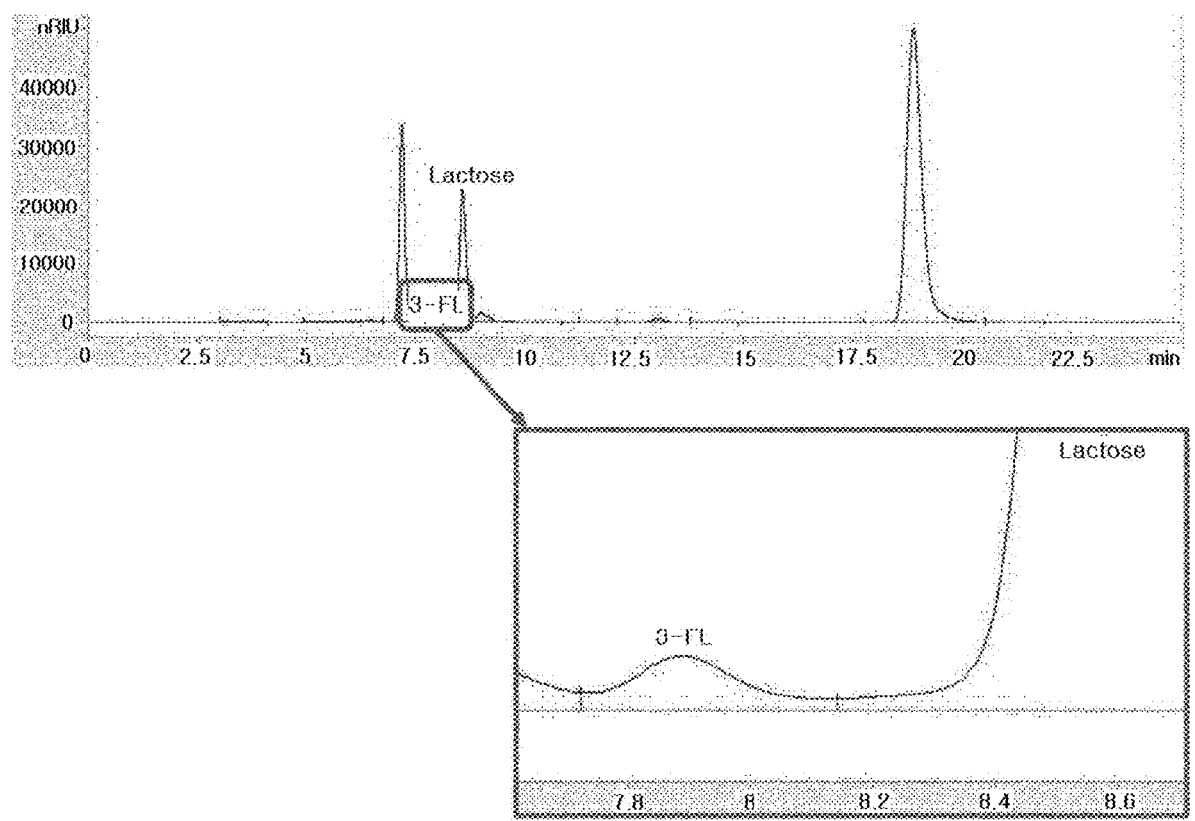
FIG. 2 shows the result of HPLC measurement of 3-fucosyllactose produced in *Corynebacterium glutamicum* pVBCL+pEGWA (pEGW+azoT)
Figure 3:
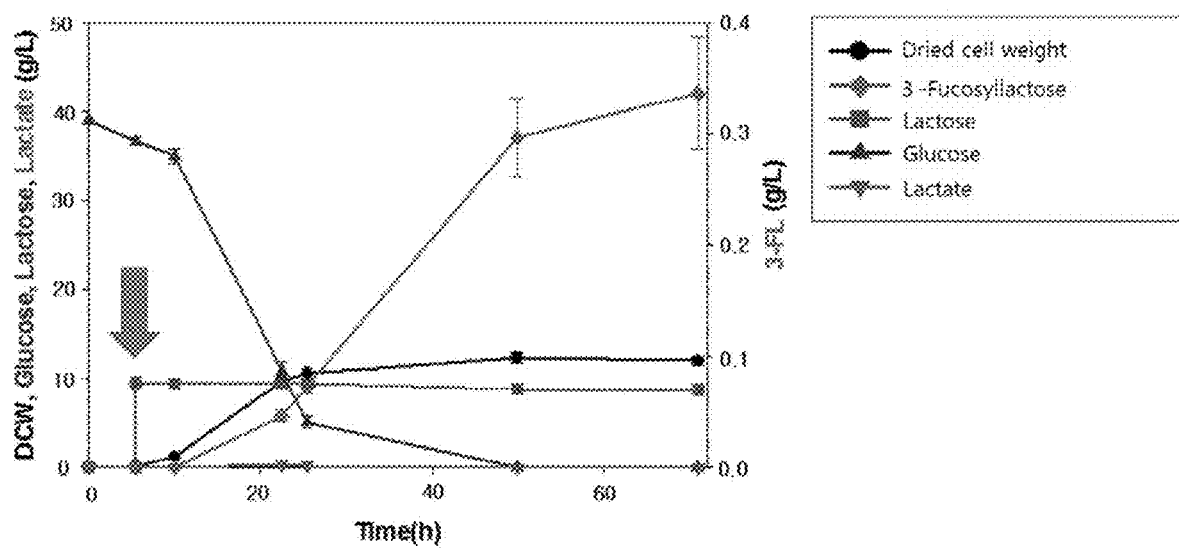
FIG. 3 is a graph showing the results of batch culture using recombinant *Corynebacterium glutamicum* (*C. glutamicum*) pVBCL+pEGWT. When optical density ($OD_{600}$) reaches about 0.8, IPTG and lactose are added to allow final concentrations to become 1.0 mM and 10 g/L (arrows). The symbols in the graph have the following meanings: ●: Dried cell weight, ▲: Glucose, ■: Lactose, ▼: Lactate, and ◆: 3-fucosyllactose.

As a result of the flask batch culture, 390 mg/L of 3-fucosyllactose was produced. The yield of 2'-fucosyllactose relative to lactose was 0.32 (moles of 2'-fucosyllactose/moles of lactose), and the productivity was 5.49 mg/L/h (see FIG. 3 and Table 4). FIG. 2 shows the result of HPLC measurement of 3-fucosyllactose produced from *Corynebacterium glutamicum* pVBCL+pEGWA (pEGW+azoT). The results of the batch culture are described in Table 4 below, and FIG. 3 shows the result of flask batch culture using recombinant *Corynebacterium glutamicum* (*C. glutamicum*) pVBCL+pEGWA.

TABLE 4

Result of flask batch culture using recombinant
*Corynebacterium glutamicum* (*C. glutamicum*) pVBCL + pEGWA

| | Final dried cell weight (g/L) | Lactose consumption[a] (g/L) | Maximum 3'-fucosyllactose concentration[a] (mg/L) | Yield (moles of 2'-fucosyllactose/ moles of lactose) | Productivity[a] (mg/L/h) |
|---|---|---|---|---|---|
| Flask | 12.0 | 0.71 | 390 | 0.38 | 5.49 |

[a]Concentration of 3'-fucosyllactose of lactose is calculated from only that present in medium.

(4) Production of 3-Fucosyllactose Through Fed-Batch Culture

In order to produce high-concentration 3-fucosyllactose through high-concentration cell culture, fed-batch culture was conducted in a 2.5 L fermenter using recombinant *Corynebacterium glutamicum* (*C. glutamicum*) introduced with pVBCL and pEGWA plasmids.

In order to maintain cell growth from when 40 g/L glucose supplied at an initial stage was completely consumed, a feeding solution started to be supplied at a rate of 5.7 g/L/h by a continuous feeding method. At the same time, IPTG and lactose were added to induce the production of 3-fucosyllactose.

As a result of the experiment, acetic acid was found not to be produced at all during fermentation, and the dried cell weight reached 48.9 g/L due to metabolism of glucose. In addition, the maximum concentration of 3-fucosyllactose was 3.6 g/L, the yield (ratio of moles of 3-fucosyllactose to moles of lactose) was 0.17 mole/mole, and the productivity was 0.03 g/L/h (FIG. 4 and Table 5).

Figure 4:
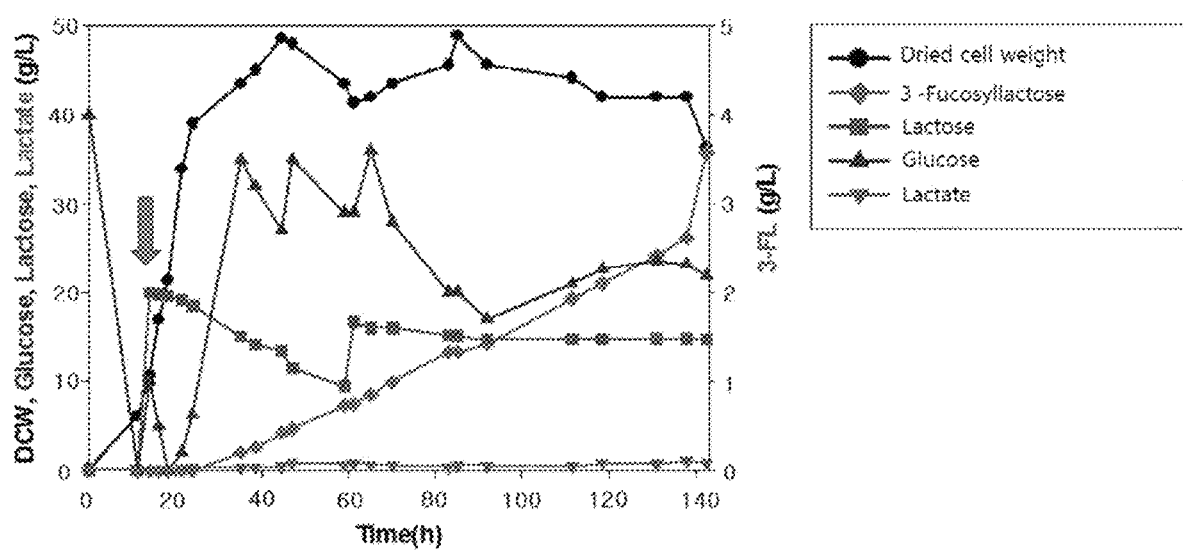
FIG. 4 is a graph showing the results of fed-batch culture using recombinant *Corynebacterium glutamicum* (*C. glutamicum*) pVBCL+pEGWT. After 40 g/L glucose, supplied at an initial stage, was completely consumed, supply of glucose through a continuous feeding method commenced. At the same time, IPTG and lactose were added (large arrows). The symbols in the graph have the following meanings: ●: Dried cell weight, ▲: Glucose, ■: Lactose, ▼: Lactate, and ◆: 3-fucosyllactose.

The results of fed-batch culture to produce 3-fucosyllactose are shown in the following Table 5, and FIG. 4 is a graph showing the results of fed-batch culture using recombinant *Corynebacterium glutamicum* pVBCL+pEGWA.

TABLE 5

Results of fed-batch culture using recombinant *Corynebacterium glutamicum* (*C. glutamicum*) pVBCL + pEGWT

| Plasmid | Final dried cell weight (g/L) | Lactose consumption[a] (g/L) | Maximum 3'-fucosyllactose concentration[a] (g/L) | Yield (moles of 3'-fucosyllactose/ moles of lactose) | Productivity[a] (g/L/h) |
|---|---|---|---|---|---|
| pVBCLpEGWA | 48.9 | 15.3 | 3.6 | 0.17 | 0.03 |

[a]Concentration of 3'-fucosyllactose of lactose is calculated from only that present in medium.
[b]3-FL productivity was calculated after IPTG induction.

The invention claimed is:

1. A method of producing 3-fucosyllactose comprising culturing in a medium supplemented with lactose a recombinant *Corynebacterium glutamicum* transformed to express α-1, 3-fucosyltransferase, transformed to express GDP-D-mannose-4, 6-dehydratase, transformed to express GDP-L-fucose synthase, and transformed to express lactose permease, and isolating 3-fucosyllactose from the medium, wherein the recombinant *Corynebacterium glutamicum* has phosphomannomutase and GTP-mannose-1-phosphate guanylyltransferase.

2. The method according to claim 1, wherein the medium further comprises glucose.

3. The method according to claim 2, wherein the production of the 3-fucosyllactose is carried out by batch culture or fed-batch culture comprising further supplying glucose or lactose.

4. The method according to claim 1, wherein the recombinant *Corynebacterium glutamicum* is transformed to overexpress phosphomannomutase, and is transformed to overexpress GTP-mannose-1-phosphate guanylyltransferase.

* * * * *

SEQUENCE LISTING

<160> NUMBER OF SEQ ID NOS: 7

<210> SEQ ID NO 1
<211> LENGTH: 1377
<212> TYPE: DNA
<213> ORGANISM: Unknown
<220> FEATURE:
<223> OTHER INFORMATION: Corynebacterium glutamicum ATCC 13032

<400> SEQUENCE: 1

```
atgcgtaccc gtgaatctgt cacggctgta attaaggcgt atgacgtccg tggtgttgtt      60
ggtgtcgata ttgatgctga tttcatttct gagactggcg ctgcctttgg tcggctcatg     120
cgtagtgagg gtgaaaccac cgttgctatt ggccatgaca tgcgtgattc ctcccctgaa     180
ttggccaagg cgtttgccga tggcgtgact gcacagggtt tggatgttgt tcatttggga     240
ctgacttcta ctgatgagct gtactttgcg tccggaacct tgaagtgtgc tggtgcgatg     300
tttactgcgt cgcataaccc cgctgagtac aacggcatca agttgtgtcg tgcgggtgct     360
cgtccggtcg gtcaggattc tggtttggcc aacatcattg atgatctggt tgagggtgtt     420
ccagcgtttg atggtgagtc aggttcggtt tctgagcagg atttgctgag cgcatatgcc     480
gagtacctca atgagcttgt tgatctgaag aacatccgcc cgttgaaggt tgctgtggat     540
gcggcaaacg gcatgggtgg gttcactgtc cctgaggtat tcaagggtct gccacttgat     600
gttgcgccac tgtattttga gcttgacggc aatttcccca accatgaggc caatcctctg     660
gagcctgcca acctggttga tttgcagaag tttaccgtag agaccggatc tgatatcggt     720
ttggcgttcg acggcgatgc ggatcgttgc ttcgtggtcg atgagaaggg ccagccagtc     780
agcccttcgg cgatctgtgc gatcgtagcg gagcgttact tggagaagct tccgggttcc     840
accatcatcc acaacctgat tacctctaag gctgtgcctg aggtgattgc tgaaaacggt     900
ggcactgcgg tgcgtactcg cgtgggtcac tccttcatca aggcgaagat ggcagagacc     960
ggtgcggcct ttggtggcga gcactctgcg cactactact tcactgagtt cttcaatgcg    1020
gactccggca ttttggctgc gatgcacgtg ctggctgcgc tgggaagcca ggaccagcca    1080
ctcagtgaga tgatggctag gtataaccgg tacgttgctt caggcgagtt gaactcccgt    1140
ttggctaatg cagaggcgca gcaagagcgc acccaggctg tgctcgatgc gttcgctgat    1200
cgcaccgagt ccgtggacac ccttgacggc gtgactgtgg aactcaagga cacctccgcg    1260
tggttcaacg tgcgtgcgtc caacaccgag ccgctgcttc gcctcaatgt tgaagctgca    1320
```

```
tcgaaggaag aagtcgatgc gttggtagcg gagattctag ggattatccg cgcataa      1377
```

```
<210> SEQ ID NO 2
<211> LENGTH: 1089
<212> TYPE: DNA
<213> ORGANISM: Unknown
<220> FEATURE:
<223> OTHER INFORMATION: Corynebacterium glutamicum ATCC 13032

<400> SEQUENCE: 2
atgactttaa ctgacaacag caaaaacgtt gatgctgtca tcttggtcgg tggcaaaggt      60
acccgactgc gccccctgac cgtcaatact ccaaagccaa tgctgccaac tgctggccac     120
ccattcttga cccacctttt ggcccgcatc aaggccgcag gcatcacaca cgtcgtgctg     180
ggaacgtcat tcaaagctga agtcttcgag gaatacttcg gagatggctc cgaaatgggc     240
ttggaaattg aatatgtcgt cgaggatcag cctttgggca ctggtggtgg catccgaaac     300
gtctacgaca gctgcgtca cgatactgcg attgtgttca acggcgatgt gctctccggt     360
gcggatctca acagcattct ggacacccac cgcgaaaagg acgcagatct gaccatgcat     420
ctcgtgcgcg tagctaaccc tcgtgcgttt ggttgcgtcc ccaccgatga ggatggtcgc     480
gtcagcgaat tccttgaaaa gaccgaagat ccaccaaccg atcagatcaa cgccggctgc     540
tacgtgttca agaaggaact catcgagcag atcccggcag gccgagcagt ttccgtcgag     600
cgcgaaacct tccctcagct gttggaagaa ggcaagcgag tcttcggcca cgtcgacgct     660
tcctactggc gcgacatggg cacccccaagc gacttcgtcc gcggctcggc tgacctggtc     720
cgcggcattg cgtactcccc cattgctcgaa ggcaaaacag gagagtcgct tgtcgacgcc     780
tccgccggcg ttcgcgacgg cgtcctgctg ctcggcggaa ccgtagtcgg ccgcggcact     840
gagatcggtg ccggctgccg cgttgacaac actgttattt tcgacggcgt caccattgaa     900
ccaggtgcgg tcattgaaaa ttccatcatt cctcgggag cacgcatcgg tgctaatgcg     960
cacatctccg gttgcatcat tggcgagggc gcacaggttg gtgctcggtg tgaactcaac    1020
gcagggatgc gcgtcttccc aggcgttgtg atcccagaca gcggaattcg ttttccgtct    1080
gatcagtag                                                            1089
```

```
<210> SEQ ID NO 3
<211> LENGTH: 2090
<212> TYPE: DNA
<213> ORGANISM: Unknown
<220> FEATURE:
<223> OTHER INFORMATION: E.coli K-12 MG1655

<400> SEQUENCE: 3
atgtcaaaag tcgctctcat caccggtgta accggacaag acggttctta cctggcagag      60
tttctgctgg aaaaaggtta cgaggtgcat ggtattaagc gtcgcgcatc gtcattcaac     120
accgagcgcg tggatcacat ttatcaggat ccgcacacct gcaacccgaa attccatctg     180
cattatggcg acctgagtga tacctctaac ctgacgcgca ttttgcgtga agtacagccg     240
gatgaagtgt acaacctggg cgcaatgagc cacgttgcgg tctcttttga gtcaccagaa     300
tataccgctg acgtcgacgc gatgggtacg ctgcgcctgc tggaggcgat ccgcttcctc     360
ggtctggaaa agaaaactcg tttctatcag gcttccacct ctgaactgta tggtctggtg     420
caggaaattc cgcagaaaga gaccacgccg ttctacccgc gatctccgta tgcggtcgcc     480
aaactgtacg cctactggat caccgttaac taccgtgaat cctacggcat gtacgcctgt     540
```

```
aacggaattc tcttcaacca tgaatccccg cgccgcggcg aaaccttcgt tacccgcaaa      600
atcacccgcg caatcgccaa catcgcccag gggctggagt cgtgcctgta cctcggcaat      660
atggattccc tgcgtgactg gggccacgcc aaagactacg taaaaatgca gtggatgatg      720
ctgcagcagg aacagccgga agatttcgtt atcgcgaccg gcgttcagta ctccgtgcgt      780
cagttcgtgg aaatggcggc agcacagctg gcatcaaac tgcgctttga aggcacgggc       840
gttgaagaga agggcattgt ggtttccgtc accgggcatg acgcgccggg cgttaaaccg      900
ggtgatgtga ttatcgctgt tgacccgcgt tacttccgtc cggctgaagt tgaaacgctg      960
ctcggcgacc cgaccaaagc gcacgaaaaa ctgggctgga accggaaat cacccctcaga     1020
gagatggtgt ctgaaatggt ggctaatgac ctcgaagcgg cgaaaaaaca ctctctgctg     1080
aaatctcacg gctacgacgt ggcgatcgcg ctggagtcat aagcatgagt aaacaacgag     1140
ttttattgc tggtcatcgc gggatggtcg gttccgccat caggcggcag ctcgaacagc      1200
gcggtgatgt ggaactggta ttacgcaccc gcgacgagct gaacctgctg acagccgcg     1260
ccgtgcatga tttctttgcc agcgaacgta ttgaccaggt ctatctggcg gcggcgaaag     1320
tgggcggcat tgttgccaac aacacctatc cggcggattt catctaccag aacatgatga     1380
ttgagagcaa catcattcac gccgcgcatc agaacgacgt gaacaaactg ctgtttctcg     1440
gatcgtcctg catctacccg aaactggcaa acagccgat ggcagaaagc gagttgttgc      1500
agggcacgct ggagccgact aacgagcctt atgctattgc caaaatcgcc gggatcaaac     1560
tgtgcgaatc atacaaccgc cagtacggac gcgattaccg ctcagtcatg ccgaccaacc     1620
tgtacgggcc acacgacaac ttccacccga gtaattcgca tgtgatccca gcattgctgc     1680
gtcgcttcca cgaggcgacg gcacagaatg cgccggacgt ggtggtatgg ggcagcggta     1740
caccgatgcg cgaatttctg cacgtcgatg atatggcggc ggcgagcatt catgtcatgg     1800
agctggcgca tgaagtctgg ctggagaaca cccagccgat gttgtcgcac attaacgtcg     1860
gcacgggcgt tgactgcact atccgcgagc tggcgcaaac catcgccaaa gtggtgggtt     1920
acaaaggccg ggtggttttt gatgccagca accggatgg cacgccgcgc aaactgctgg      1980
atgtgacgcg cctgcatcag cttggctggt atcacgaaat ctcactggaa gcggggcttg     2040
ccagcactta ccagtggttc cttgagaatc aagaccgctt tcgggggtaa                2090
```

<210> SEQ ID NO 4  
<211> LENGTH: 3335  
<212> TYPE: DNA  
<213> ORGANISM: Unknown  
<220> FEATURE:  
<223> OTHER INFORMATION: E.coli BL21star(DE3)

<400> SEQUENCE: 4

```
accatcgaat ggcgcaaaac ctttcgcggt atggcatgat agcgcccgga agagagtcaa       60
ttcagggtgg tgaatgtgaa accagtaacg ttatacgatg tcgcagagta tgccggtgtc      120
tcttatcaga ccgtttcccg cgtggtgaac caggccagcc acgtttctgc gaaaacgcgg      180
gaaaaagtgg aagcggcgat ggcggagctg aattacattc ccaaccgcgt ggcacaacaa      240
ctggcgggca aacagtcgtt gctgattggc gttgccacct ccagtctggc cctgcacgcg      300
ccgtcgcaaa ttgtcgcggc gattaaatct cgcgccgatc aactgggtgc cagcgtggtg      360
gtgtcgatgg tagaacgaag cggcgtcgaa gcctgtaaag cggcggtgca caatcttctc      420
gcgcaacgcg tcagtgggct gatcattaac tatccgctgg atgaccagga tgccattgct     480
gtggaagctg cctgcactaa tgttccggcg ttatttcttg atgtctctga ccagacaccc     540
```

```
atcaacagta ttattttctc ccatgaagac ggtacgcgac tgggcgtgga gcatctggtc    600
gcattgggtc accagcaaat cgcgctgtta gcgggcccat taagttctgt ctcggcgcgt    660
ctgcgtctgg ctggctggca taaatatctc actcgcaatc aaattcagcc gatagcggaa    720
cgggaaggcg actggagtgc catgtccggt tttcaacaaa ccatgcaaat gctgaatgag    780
ggcatcgttc ccactgcgat gctggttgcc aacgatcaga tggcgctggg cgcaatgcgc    840
gccattaccg agtccgggct gcgcgttggt gcggatatct cggtagtggg atacgacgat    900
accgaagaca gctcatgtta tcccgccgcc ttaaccacca tcaaacagga ttttcgcctg    960
ctggggcaaa ccagcgtgga ccgcttgctg caactctctc agggccaggc ggtgaagggc   1020
aatcagctgt tgcccgtctc actggtgaaa agaaaaacca ccctggcgcc caatacgcaa   1080
accgcctctc cccgcgcgtt ggccgattca ttaatgcagc tggcacgaca ggtttcccga   1140
ctggaaagcg ggcagtgagc gcaacgcaat taatgtgagt tagctcactc attaggcacc   1200
ccaggcttta cactttatgc ttccggctcg tatgttgtgt ggaattgtga gcggataaca   1260
atttcacaca ggaaacagct atgtactatt taaaaaacac aaacttttgg atgttcggtt   1320
tattcttttt cttttacttt tttatcatgg gagcctactt cccgttttc ccgatttggc    1380 tacatgacat caaccatatc agcaaaagtg atacgggtat tattttttgcc gctatttctc   1440 tgttctcgct attattccaa ccgctgtttg gtctgctttc tgacaaactc gggctgcgca   1500
aatacctgct gtggattatt accggcatgt tagtgatgtt tgcgccgttc tttatttta    1560 tcttcgggcc actgttacaa tacaacattt tagtaggatc gattgttggt ggtatttatc   1620
taggcttttg ttttaacgcc ggtgcgccag cagtagaggc atttattgag aaagtcagcc   1680
gtcgcagtaa tttcgaattt ggtcgcgcgc ggatgtttgg ctgtgttggc tgggcgctgt   1740
gtgcctcgat tgtcggcatc atgttcacca tcaataatca gtttgttttc tggctgggct   1800
ctggctgtgc actcatcctc gccgttttac tcttttttcgc caaaacggat gcgccctctt   1860
ctgccacggt tgccaatgcg gtaggtgcca accattcggc atttagcctt aagctggcac   1920
tggaactgtt cagacagcca aaactgtggt ttttgtcact gtatgttatt ggcgtttcct   1980
gcacctacga tgttttttgac caacagtttg ctaatttctt tacttcgttc tttgctaccg   2040
gtgaacaggg tacgcgggta tttggctacg taacgacaat gggcgaatta cttaacgcct   2100
cgattatgtt ctttgcgcca ctgatcatta atcgcatcgg tgggaaaaac gccctgctgc   2160
tggctggcac tattatgtct gtacgtatta ttggctcatc gttcgccacc tcagcgctgg   2220
aagtggttat tctgaaaacg ctgcatatgt ttgaagtacc gttcctgctg gtgggctgct   2280
ttaaatatat taccagccag tttgaagtgc gttttttcagc gacgatttat ctggtctgtt   2340
tctgcttctt taagcaactg gcgatgattt ttatgtctgt actggcgggc aatatgtatg   2400
aaagcatcgg tttccagggc gcttatctgg tgctgggtct ggtggcgctg ggcttcacct   2460
taatttccgt gttcacgctt agcggccccg gcccgctttc cctgctgcgt cgtcaggtga   2520
atgaagtcgc ttaagcaatc aatgtcggat gcggcgcgag cgccttatcc gaccaacata   2580
tcataacgga gtgatcgcat tgaacatgcc aatgaccgaa agaataagag caggcaagct   2640
atttaccgat atgtgcgaag gcttaccgga aaaaagactt cgtgggaaaa cgttaatgta   2700
tgagtttaat cactcgcatc catcagaagt tgaaaaaaga gaaagcctga ttaaagaaat   2760
gtttgccacg gtaggggaaa acgcctgggt agaaccgcct gtctatttct cttacggttc   2820
caacatccat ataggccgca attttttatgc aaatttcaat ttaaccattg tcgatgacta   2880
```

```
cacggtaaca atcggtgata acgtactgat tgcacccaac gttactcttt ccgttacggg      2940
acaccctgta caccatgaat tgagaaaaaa cggcgagatg tactcttttc cgataacgat      3000
tggcaataac gtctggatcg aagtcatgt ggttattaat ccaggcgtca ccatcgggga       3060
taattctgtt attggcgcgg gtagtatcgt cacaaaagac attccaccaa acgtcgtggc      3120
ggctggcgtt ccttgtcggg ttattcgcga ataaacgac cgggataagc actattattt       3180
caaagattat aaagttgaat cgtcagttta aattataaaa attgcctgat acgctgcgct      3240
tatcaggcct acaagttcag cgatctacat tagccgcatc cggcatgaac aaagcgcagg     3300
aacaagcgtc gcatcatgcc tctttgaccc acagc                                 3335

<210> SEQ ID NO 5
<211> LENGTH: 978
<212> TYPE: DNA
<213> ORGANISM: Unknown
<220> FEATURE:
<223> OTHER INFORMATION: Azospirillum brasilense ATCC 29145

<400> SEQUENCE: 5
atgctcgatc agcggacaag cgcgtttctt gaggaattcc tggcgaagcc gggcggcgat       60
cccgagcggc tcgaccgctt cctgctgcac ggcccgtacc gcggccggcg cggcggcaaa      120
ccgcggctga agctggcctt ccacgacttc tggccggagt cgacaaggg cacgaacttc       180 ttcatcgaga tcctgtccag ccgcttcgac ctgtcggtgg tcgaggacga cagcgaccct     240
gccatcgtgt cggtcttcgg cgggcggcac cgcgaggcgc gcagccgccg caccctgttc      300
ttcaccgggg agaacgtgcg cccgccgttg acggcttcg acatggcggt gtccttcgac       360
cgcgtcgacg acccgcgcca ttaccgcctg ccgctctacg tcatgcacgc ctacgagcac      420
atgcgggagg gggcggtgcc gcatttctgt tcgccggtcc tgccgccggt gccgccgacg      480
cgggcggcct tcgcggagcg cggcttctgc gccttcctct acaagaaccc gaacggggag      540
cgccgcaacc gcttcttccc ggtgctggac gggcggcggc gcgtcgattc ggtgggctgg      600
cacctgaaca acaccggcag cgtcgtcaag atgggctggc tgtcgaagat ccgcgtcttc      660
gaacgctacc gtttcgcctt cgccttcgag aacgccagcc atcccggcta tctgacggaa     720
aagatcctgg acgtcttcca ggccggggcg gtgccgctct attggggtga tcccgacctg      780
gagcgcgagg tggcggtcgg cagcttcatc gacgtgtcgc gcttcgccac ggacgaggag      840
gcggtggacc acatccttgc ggtggacgac gattacgacg cctattgcgc ccaccgcgcc      900
gtggcgccct tcctggggac ggaggagttt tatttcgacg cctaccgcct cgccgactgg      960
atcgagagcc ggctgtaa                                                   978

<210> SEQ ID NO 6
<211> LENGTH: 54
<212> TYPE: DNA
<213> ORGANISM: Artificial Sequence
<220> FEATURE:
<223> OTHER INFORMATION: F_inf_sac1_azoT

<400> SEQUENCE: 6
gctttcgggg gtaagagctc aaggagatat acaatgctcg atcagcggac aagc            54

<210> SEQ ID NO 7
<211> LENGTH: 40
<212> TYPE: DNA
<213> ORGANISM: Artificial Sequence
<220> FEATURE:
<223> OTHER INFORMATION: R_inf_sac1_azoT
```

```
<400> SEQUENCE: 7
cggccagtga attcgagctc ttacagccgg ctctcgatcc                    40
```